United States Patent
Wu et al.

(10) Patent No.: US 11,590,361 B2
(45) Date of Patent: Feb. 28, 2023

(54) METHOD FOR CALCULATING AN OPTIMAL ARC ANGLE OF DYNAMIC ARC RADIOTHERAPY BY VOLUME-BASED ALGORITHMS

(71) Applicant: National Yang-Ming University, Taipei (TW)

(72) Inventors: Tung-Hsin Wu, Taipei (TW); Pei-Wei Shueng, Taipei (TW); Chen-Xiong Hsu, Taipei (TW); Jing-Yi Sun, Taipei (TW); Kuan-Heng Lin, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 425 days.

(21) Appl. No.: 16/818,487

(22) Filed: Mar. 13, 2020

(65) Prior Publication Data

US 2020/0289849 A1 Sep. 17, 2020

(30) Foreign Application Priority Data

Mar. 15, 2019 (TW) .................. 108108891

(51) Int. Cl.
*G06T 7/00* (2017.01)
*A61N 5/10* (2006.01)
(Continued)

(52) U.S. Cl.
CPC ......... *A61N 5/1031* (2013.01); *A61N 5/1047* (2013.01); *A61N 5/1071* (2013.01); *G06T 7/0012* (2013.01); *G06T 7/11* (2017.01); *G06T 7/136* (2017.01); *G06T 7/62* (2017.01); *A61N 2005/1055* (2013.01); *G06T 2207/10081* (2013.01); *G06T 2207/10088* (2013.01);
(Continued)

(58) Field of Classification Search
CPC .... A61N 5/1031; A61N 5/103; A61N 5/1039; A61N 5/1081; A61N 5/1067; G06T 2207/10081; G06T 2207/30096; G06T 7/0012; G06T 2207/10088; G06T 2207/10116; G06T 2207/30061; G06T 7/11; G06T 7/62
See application file for complete search history.

(56) References Cited

U.S. PATENT DOCUMENTS 10,549,121 B2 * 2/2020 Wu ................ A61N 5/1031
2018/0078784 A1 * 3/2018 Schnarr ............ A61N 5/1031
(Continued)

OTHER PUBLICATIONS

Yin, Li, et al. "Volumetric-modulated arc therapy vs c-IMRT in esophageal cancer: a treatment planning comparison." World journal of gastroenterology: WJG 18.37 (2012): 5266. (Year: 2012).*
(Continued)

*Primary Examiner* — Li Liu
(74) *Attorney, Agent, or Firm* — Muncy, Geissler, Olds & Lowe, P.C.

(57) ABSTRACT

This invention provides a method applied for the new dynamic arc radiotherapy treatment planning to calculate an optimal arc angle. With this invention, an operator without rich experience is able to reach the expected low dose in lungs easily and quickly. This invention can not only estimate the distribution of low radiation dose in lungs but also reduce the shortcomings like consumption of time and inaccuracy caused by manual trial and error.

12 Claims, 6 Drawing Sheets

(51) Int. Cl.
*G06T 7/11* (2017.01)
*G06T 7/136* (2017.01)
*G06T 7/62* (2017.01)

(52) U.S. Cl.
CPC ............... *G06T 2207/30061* (2013.01); *G06T 2207/30096* (2013.01)

(56) References Cited

U.S. PATENT DOCUMENTS

| | | | | |
|---|---|---|---|---|
| 2018/0369611 A1* | 12/2018 | Owens | .................. | A61N 5/1064 |
| 2019/0022409 A1* | 1/2019 | Vanderstraten | ...... | A61N 5/1081 |
| 2020/0286601 A1* | 9/2020 | Khuntia | .................. | G16H 20/00 |
| 2021/0154494 A1* | 5/2021 | Maurer | .................. | G06N 20/00 |

OTHER PUBLICATIONS

Marks, Lawrence B., et al. "Radiation dose—volume effects in the lung." International Journal of Radiation Oncology* Biology* Physics 76.3 (2010): S70-S76. (Year: 2010).*

* cited by examiner

Substituting a value set comprising a thoracic transverse diameter, a transverse diameter of a radiotherapy planning target volume and a longitudinal length of a radiotherapy planning target volume in a medical image including a thoracic cavity into a restricted volume radius algorithm to calculate a radius of a unilateral restricted volume and a radius of the other unilateral restricted volume

↓

Substituting the radius of the unilateral restricted volume, the radius of the other unilateral restricted volume and a desired value of low radiation dose (5 Gy) in lungs $V_5$ into a restricted volume algorithm to obtain a unilateral restricted volume

↓

Substituting the radius of the unilateral restricted volume, the radius of the other unilateral restricted volume and the desired value of low radiation dose (5 Gy) in lungs $V_5$ into the restricted volume algorithm to obtain the other unilateral restricted volume

↓

Substituting the unilateral restricted volume and the other unilateral restricted volume into a volume-based algorithm respectively to obtain a unilateral restricted angle and the other unilateral restricted angle

↓

Subtracting the unilateral restricted angle and the other unilateral restricted angle from 360 degrees leaves the optimal arc angle

METHOD FOR CALCULATING AN OPTIMAL ARC ANGLE OF DYNAMIC ARC RADIOTHERAPY BY VOLUME-BASED ALGORITHMS

BACKGROUND OF THE INVENTION

Technical Field of the Invention

The present invention relates to a method for calculating an optimal arc angle of dynamic arc radiotherapy. More particularly, the method is for calculating an arc angle by a volume-based algorithm.

Background

Cancer has been the first place of the top ten causes of death in Taiwan for the past decades. Although people pay much more attention on how to prevent cancer recently, the incidence rate of malignant tumor is still increasing. And nearly half of cancer patients received radiotherapy, which showed that radiotherapy is a crucial role in cancer treatment plans. In view of the cancer type and location of malignant tumor, there are critical organs, such as liver, lung heart, spinal cord, etc., surrounding around lung cancers, esophageal cancers, liver cancers or pancreatic cancers. In addition, in patients who receive radiotherapy for the malignant tumor located in thoracic cavity, there is a higher chance to have post-treatment side effects such as radiation pneumonitis, radiation pericarditis, or cardiac cell fibrosis caused by irreversible myocardial cell deformation. Therefore, how to deliver sufficient radiation doses to the malignant tumor and lower the radiation doses to the critical organs at the same time for reducing the incidence of side effects and making the critical organs meet their constraint dose which is the major goal in radiotherapy treatment planning (RTP).

With the advancement of radiotherapy technology, the current technique such as volumetric-modulated arc therapy (VMAT) and tomotherapy use the dynamic arc radiotherapy, which a linear accelerator gantry keeps irradiating while it alters beam angles continuously rotating to the isocenter of tumor in 360 degree and conducting intensity-modulated radiation therapy. Compared to the traditional radiotherapy, dynamic arc radiotherapy has a better tumor conformity and a more even radiation dose toward tumor. However, the better tumor conformity results in more beam angles, and it increases the risk of organs, healthy lungs, heart and spinal cord, for receiving an excessive amount of radiation dose. Therefore, the above reasons highlight the importance of choosing an optimal arc angle and does limit.

For a current standard RTP, physicians have to delineate the location of tumor and the field need to be treated in detail. And medical physicists draw the regions of critical organs. This process, called delineating and labeling organs, collecting the information like size, location of organs for a treatment planning platform to calculate how to treat tumor effectively and avoid harming healthy organs at the same time. Therefore, in current computed RTP of the new radiotherapy, an arc angle and a constraint dose are designed and set manually by radiation oncologists and medical physicists with their clinical experiences, and it takes a lot of repeating calculation tests and analyses to obtain an optimal arc angle which achieves the expected optimal lung radiation distribution. The whole process is time-consuming and may have artificial errors.

Taking thoracic radiotherapy as an example, in the evaluation of lung radiation dose, there is an article indicating that the incidence of radiation pneumonitis positively correlates with the irradiated volume of lung receiving above 20 Gray (Gy) radiation does ($V_{20}$) (Delaney, G., et al., Cancer, 104(6): p. 1129-37, 2005). Another reference also suggests that reducing the irradiated volume of lung decreases the risk of lung complications in patients receiving 15 Gy radiation dose (Hsu, F. M., et al., Ann Surg Oncol, 16(6): p. 1669-77, 2009). Furthermore, it is suggested that protecting more volume of lungs from receiving above 5 Gy radiation does ($V_5$) is highly associated with the incidence of reducing radiation pneumonitis (Wang, S., et al., Int J Radiat Oncol Biol Phys, 66(5): p. 1399-407, 2006).

The present invention provides a method using a volume-based algorithm that segments the volume of organs in a medical image and setting a minimum desired radiation dose of critical organ (such as lungs) to calculate an optimal arc angle.

SUMMARY OF INVENTION

The present invention discloses a method comprising setting the distribution of the low radiation dose in lungs and calculating an optimal arc angle. Therefore, radiation oncologists and medical physicists can predict the distribution of the low radiation dose in lungs before the radiotherapy treatment planning process and select the optimal arc angle in radiotherapy treatment planning. Even inexperienced personnel can use the method provided by the present invention to reach the desired distribution of the low radiation dose in lungs and improve the conventional time-consuming way or operating with artificial error.

Accordingly, the present invention provides a method for rapidly calculating an optimal arc angle used in a computerized dynamic arc radiotherapy, the method comprises delineating organs, segmenting the volume of critical organs, substituting the segmented volume and the desired value of low radiation dose in lungs, particularly the lung $V_5$, into an algorithm to obtain an optimal arc angle which can be used in an arc radiotherapy for restricting the radiation dose in lungs to the desired constraint value. The present invention can be applied to any dynamic arc radiotherapy planning, wherein the radiotherapy including photon therapy, proton therapy, heavy particle therapy.

In one embodiment of the present invention, the radiotherapy planning target and the critical organs in a computed dynamic arc radiotherapy treatment planning is an esophageal cancer and a pair of lungs respectively. According to the radiated region of the lungs, the volume of the lungs is segmented into the "out-of-field volume" of the left and right lungs and the "in-field volume" of the left and right lungs. In the other embodiment of the present invention, the width and longitudinal length of the radiotherapy planning target and the thoracic width are measured by the Euclid distance and calculated by a calculation algorithm to obtain a radius of a restricted volume ($V_{RES}$), the non-radiated volume of the in-field lungs. In another embodiment of the present invention, the radius of the right or left restricted volume ($V_{RESR}$ or $V_{RESL}$) is obtained by substituting the volume of the left and right out-of-field lungs and the desired value of low radiation dose (5 Gy) in lungs, so called $V_5$ value, into an algorithm, and a left or right restricted angle is obtained by another algorithm; furthermore, an optimal arc angle can be derived from the left or right restricted angle.

BRIEF DESCRIPTION OF THE DRAWINGS

FIG. 2A-2C are the cross-sectional, coronal and sagittal sections of the computed tomography images; FIG. 2D-2F are the cross-sectional, coronal and sagittal sections of segmented computed tomography images according to the gray scale value distribution obtained by the threshold method, and the segmented lung region is marked as pink.

In FIG. 3A, the light blue circle is a clinical target, the red circle indicates a radiotherapy planning target (tumor), the blue circle is lungs, the green circle is a heart, the pink circle is a spinal cord and the yellow circle is a region expanded outward from the radiotherapy planning target (tumor) for 2 cm; in FIG. 3B, the red region is the radiotherapy planning target (tumor) volume (PTV). A width of the tumor (F), a longitudinal length of the tumor (Lt) and a width of the thorax (T) are measured by the Euclid distance and substituted into an algorithm for obtaining a radius of a restricted volume (R).

FIG. 4 illustrates the definition of each parameter in the volume-based algorithm of the present invention. In the FIG. 4A, cross-sectional image, the light blue circle is a clinical target volume, the red region is a radiotherapy planning target (tumor) volume (PTV), the blue circle is volume of lungs, the purple region is a restricted volume of the right lung ($V_{RESR}$), the yellow region is a restricted volume of the left lung ($V_{RESL}$), the green circle is volume of a heart, the pink circle is a spinal cord volume; furthermore, a non-radiated volume ($V_{NR}$) is the sum of the restricted volume and the volume of the out-of-field lungs ($V_{OW}$); and the radiated volume is the black region of the lungs. In the FIG. 4B, the green region is volume of the right out-of-field lungs ($V_{OR}$), the dark blue region is volume of the left out-of-field lungs ($V_{OL}$), the red region is the radiotherapy planning target (tumor) volume (PTV), the purple region is the restricted volume of the right lung ($V_{RESR}$), the yellow region is a restricted volume of the left lung ($V_{RESL}$), and the green circle is heart volume.

FIG. 5 illustrates the definition of the arc angle ($\theta_A$) and the restricted angel ($\theta_{RES}$). The arc angle is an angle that a gantry of a radiotherapy equipment rotates around an iso-center, the radiotherapy planning target (PTV) centroid, to radiate. And the remaining angle, named the restricted angel, is the angle that the radiation is restricted. The arc angle plus the restricted angle equals complete 360 degrees. Normally, if $\theta_A$ is less than 60 degrees, a patient will not be suggested to have an arc radiotherapy treatment. As a result, $\theta_A$ is from 60 degrees to 360 degrees, and $\theta_{RES}$ is from 0 degree to 300 degrees. A volume of left lung ($V_L$), a volume of right lung ($V_R$), a length of the tumor (Lt) and a radius of a restricted volume (R) are used for calculating a volume of the left out-of-field lungs ($V_{OL}$), a volume of the right out-of-field lungs ($V_{OR}$), and the restricted volume of the right and left lung ($V_{RESR}$ and $V_{RESL}$). In the final step defining a desired value of low radiation dose in lungs $V_5$, substituting the above values into the following formula:

$$V_{RESR} + V_{OR} = V_R \times (1 - \text{desired } V_5),$$

$$V_{RESL} + V_{OL} = V_L \times (1 - \text{desired } V_5),$$

-continued $$V_{RESR} = \pi R^2 \frac{\theta_{RESR}}{360°}(Lt + 4),$$

$$V_{RESL} = \pi R^2 \frac{\theta_{RESL}}{360°}(Lt + 4),$$

$$\theta_A + \theta_{RESL} + \theta_{RESR} = 360°,$$

to calculate the restricted angles $\theta_{RESL}$ and $\theta_{RESR}$ needed for $V_{RESR}$ and $V_{RESL}$ calculation. And as a result, 360 degrees minus $\theta_{RESL}$ and $\theta_{RESR}$ leaves an optimal arc angle $\theta_A$.

FIG. 6A and 6B exhibit the dose distribution and DVH of various organs in thoracic cavity without applying an optimal arc angle and dose limit; on the other hand, FIG. 6C and 6D display the dose distribution and DVH of various organs in thoracic cavity when an optimal arc angle is applied with no dose limit. Furthermore, FIG. 6E and 6F show the dose distribution and DVH of various organs in thoracic cavity when an optimal arc angle is applied with a dose limit. Compared to the DVH without applying optimal arc angle, it is obvious that the desired value of low radiation dose in lungs, desired $V_5$, in the DVH of adapting an optimal angle ($\theta_A$) drops to 55%, and if it is set with a dose limit, $V_5$ value of lung can be reduced to 45%.

DETAILED DESCRIPTION OF THE INVENTION

Unless further defined, the technical terms and scientific terms used in the specification are the definitions that are generally known to those of ordinary skill in the art.

The present invention is further illustrated by the following embodiments, which are intended to be illustrative only and no to limit the scope of the invention.

In certain embodiments of the present invention, the radiotherapy target is esophageal cancer, and the location of the tumor can be at upper, middle and lower segments, and left or right side of the esophagus. The esophageal cancer generally locates in the center of the thoracic cavity, and the low dose radiation tends to affect the surrounding organs, such as lungs, heart, liver, thyroid, etc. Therefore, the embodiment demonstrates the diversity of the volume-based algorithms of the present invention.

EXAMPLE 1

A Method for Calculating an Optimal Arc Angle

Figure 1:
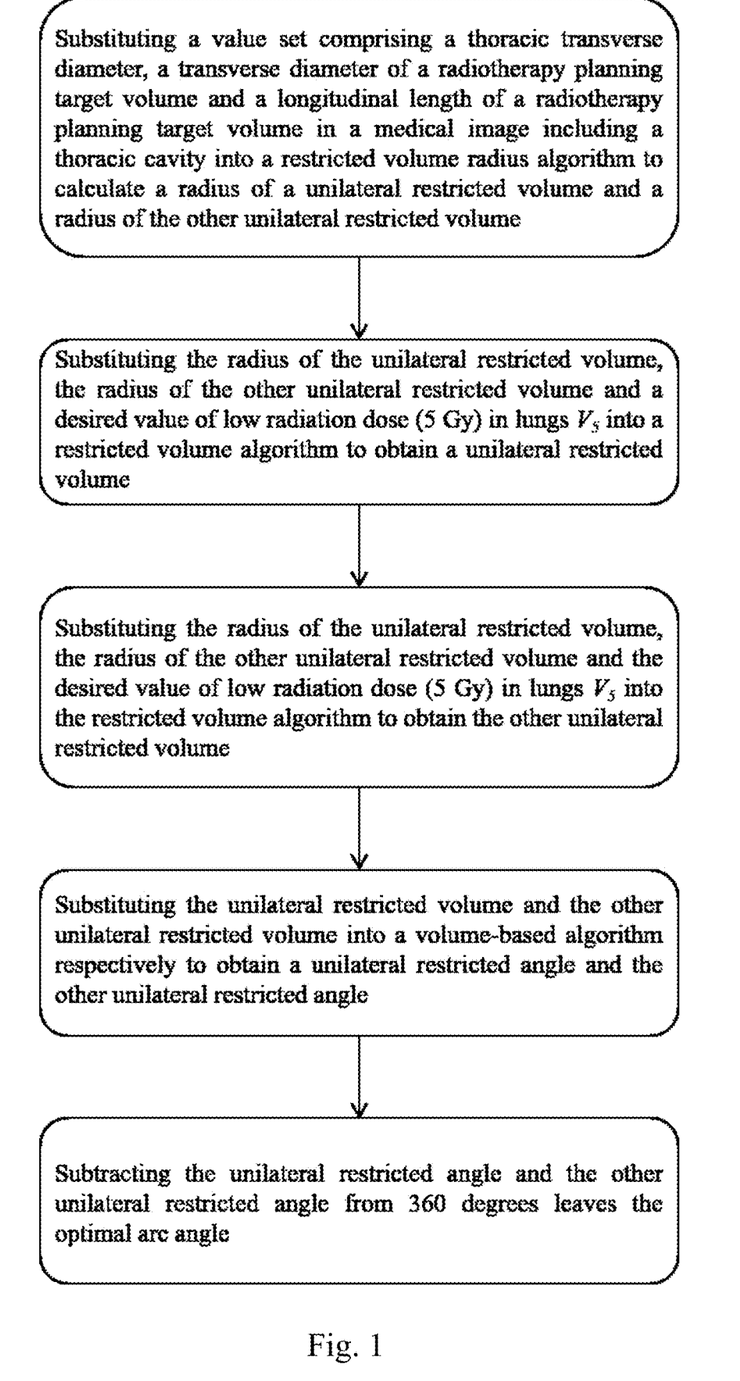
FIG. 1 is a flowchart of one embodiment of the present invention for calculating an optimal arc angle by a volume-based algorithm.

A method using volume-based algorithms of the present invention for calculating an optimal arc angle is demonstrated in this example, and a schematic flow thereof is shown in FIG. 1. The processing steps and numerical calculation procedures included in the method are detailed as follows.

Segmenting Lung Volumes in Computed Tomography Images

Figure 2:
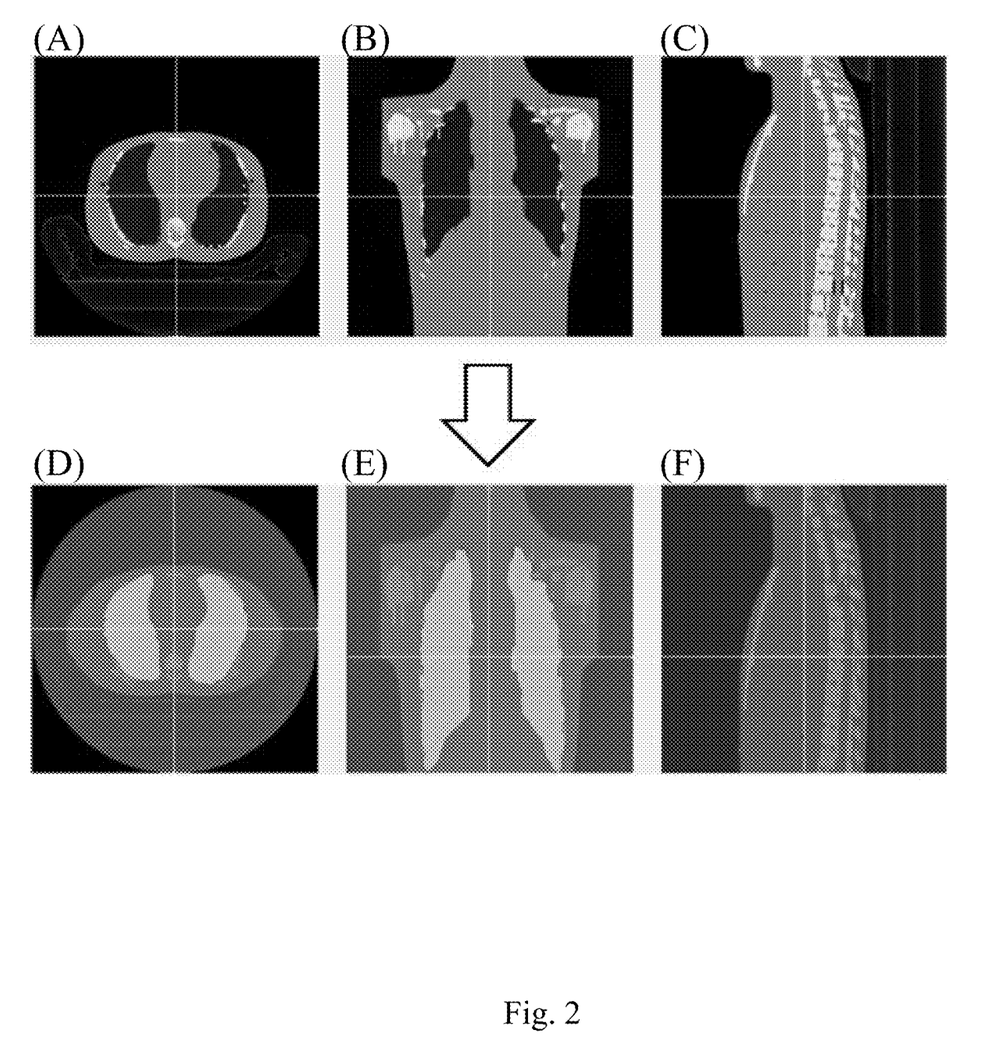
FIG. 2 displays one embodiment of the present invention for segmenting the volume of lungs in computed tomography images.

Medical images are composed of a plurality of pixels with different grayscale values. Therefore, a threshold method is used for image segmentation based on the distribution of the image grayscale value, and the different feature thresholds are set by the Otsu method. If the values of pixels match the set thresholds, the pixels are retained; however, if it does not match, the pixels are removed. By means of this, the boundary between the silhouette of the lungs and the air in the lungs is defined, so that the segmenting volume step of the lungs is accomplished (as shown in FIG. 2).

Figure 3:
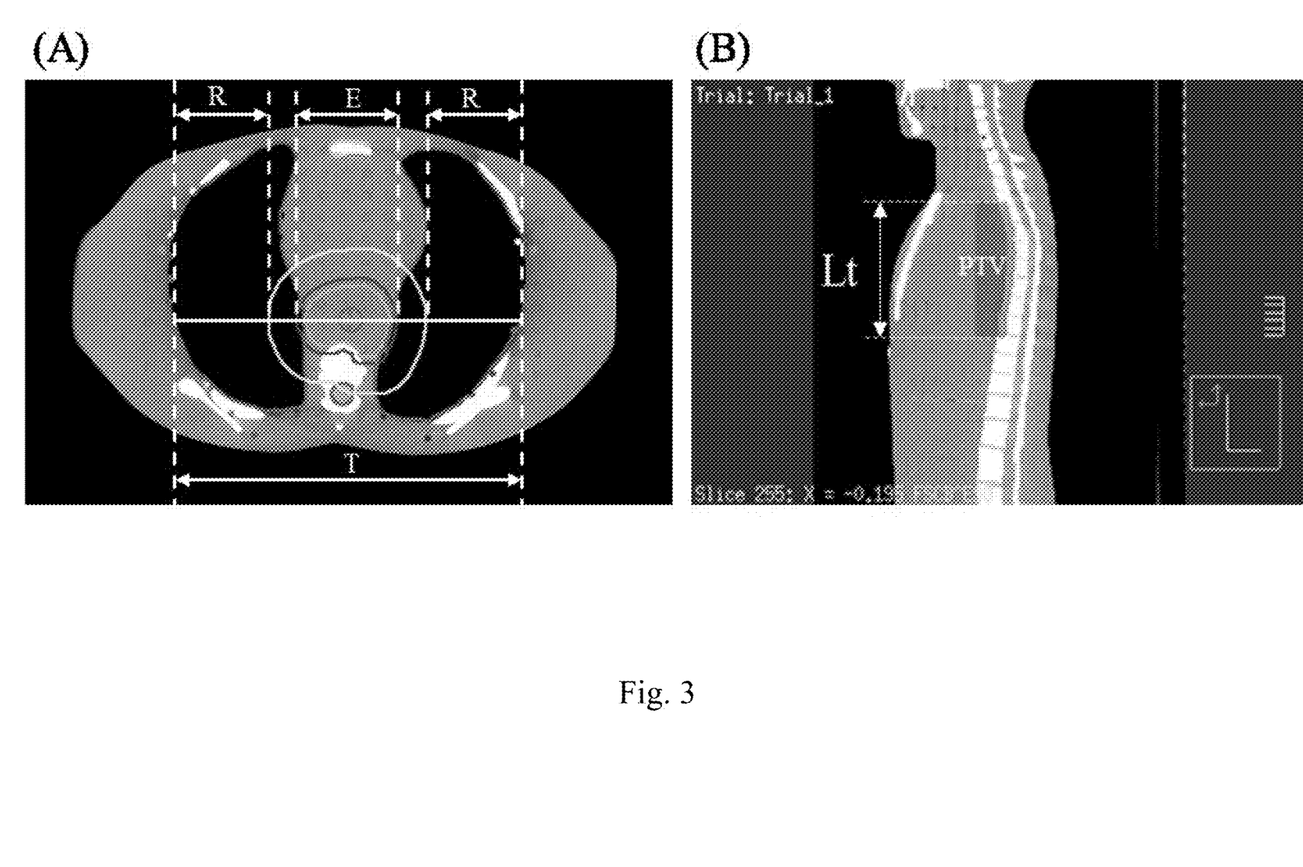
FIG. 3 shows one embodiment of the present invention for labeling the different regions in a thoracic medical image, and the FIG. 3A and 3B are cross-sectional and sagittal section images respectively.

Defining and Calculating Parameters of Tumors and Organs in Computed Tomography Images In this embodiment, the medical image is a thoracic cavity computed tomography image. In its transverse section (FIG. 3A) and the sagittal section (FIG. 3B), a thoracic transverse diameter (T), a transverse diameter of radiotherapy planning target (E) and a longitudinal length of radiotherapy planning target (Lt) are measured and defined by Euclid distance, and then these parameters are substituted into a restricted volume radius algorithm to calculate a radius of restricted volume (R). In this embodiment, the restricted volume is a lung volume; wherein the restricted volume radius algorithm is $$R = \frac{T - E - 4}{2},$$

wherein R is the radius of the unilateral restricted volume or the radius of the other unilateral restricted volume, T is the thoracic transverse diameter and E is a transverse diameter of radiotherapy planning target volume.

Defining a Restricted Volume ($V_{RES}$) and a Non-Radiated Volume ($V_{NR}$)

Figure 4:
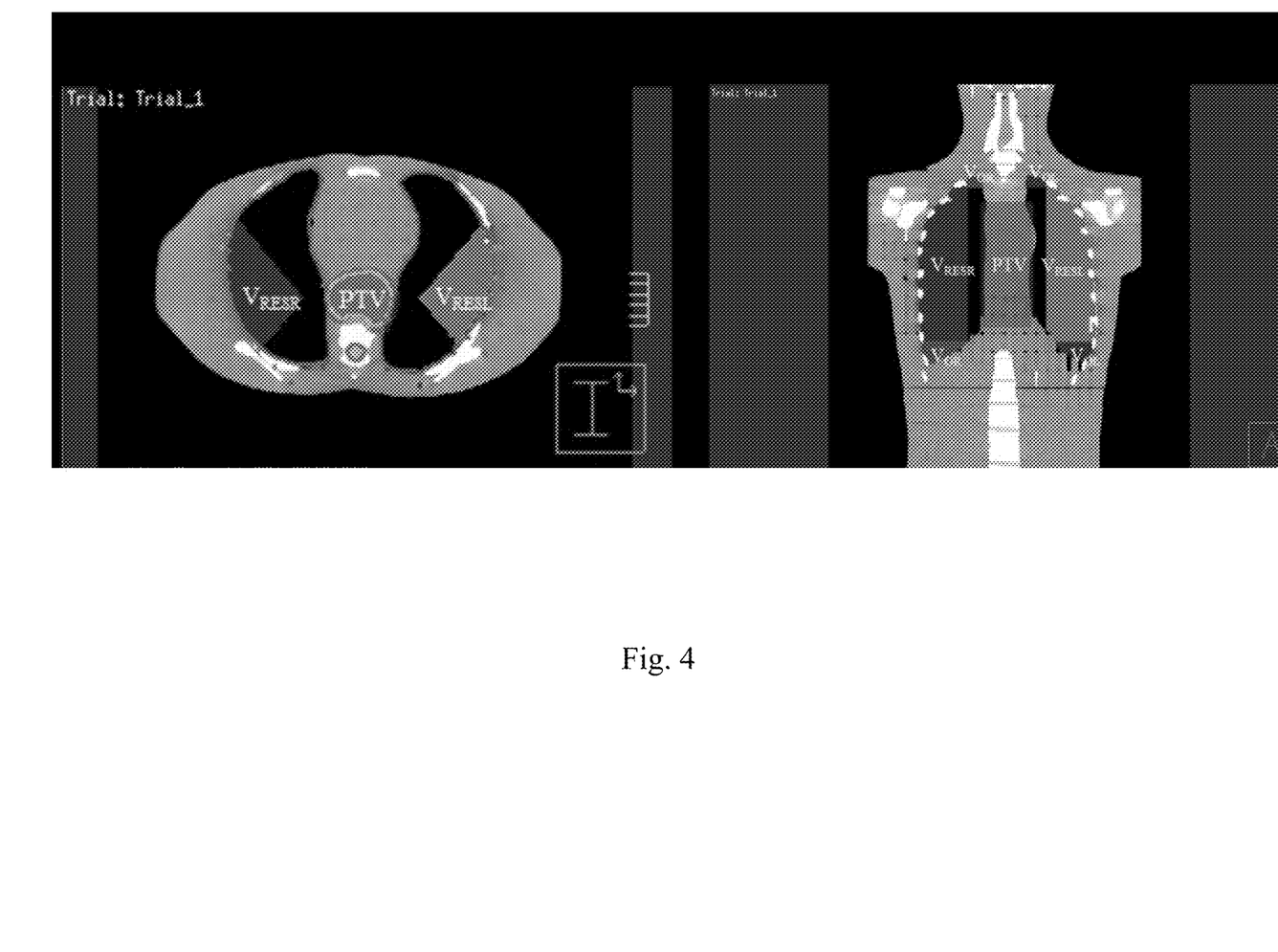
Figure 5:
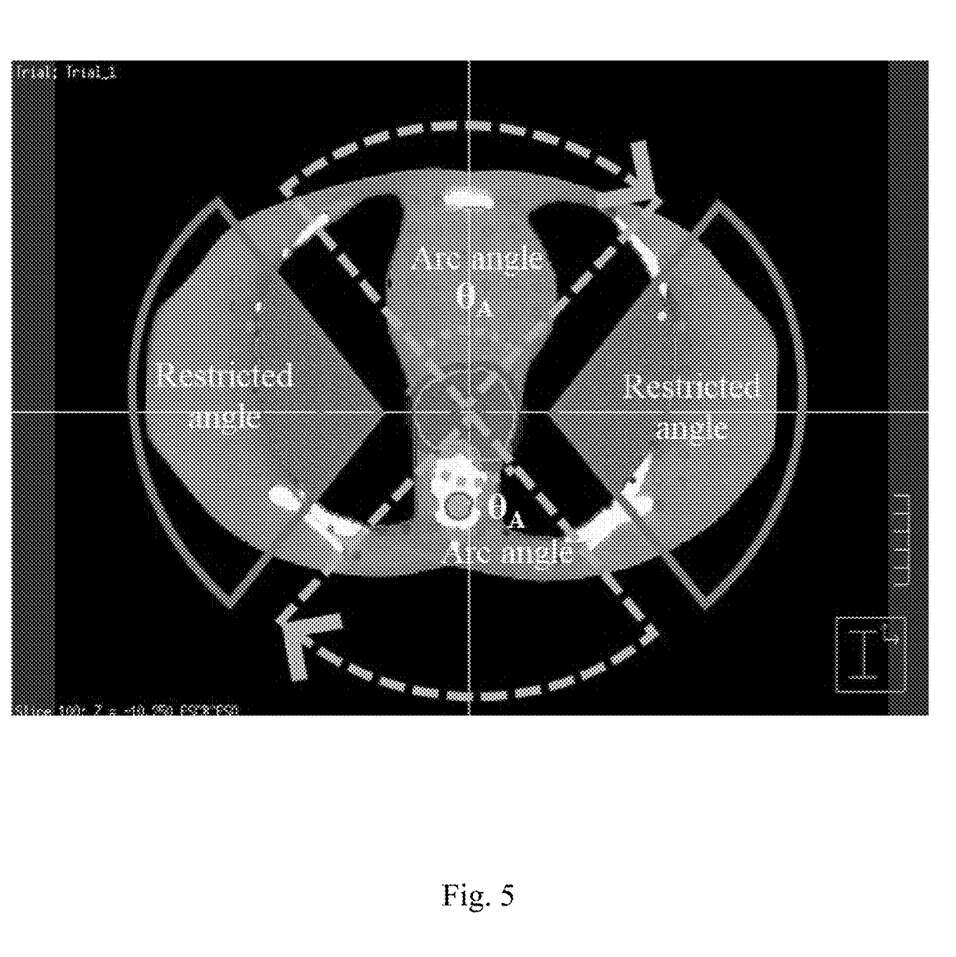

In this embodiment, the medical image is a thoracic cavity computed tomography image. According to the field range of a radiation therapy (as shown in FIG. 4), the total lung volume (V) can be divided into the out-of-field lungs volume ($V_{OW}$), a restricted volume ($V_{RES}$) and a radiated lung volume. The out-of-field lungs volume plus the restricted volume equals a non-radiated volume ($V_{NR}$), and the restricted volume can be further divided into a restricted volume of the right lung ($V_{RESR}$) and the restricted volume of the left lung ($V_{RES}$).

Calculating an Optimal Arc Angle

After segmenting the lung volume, a series of algorithms is used to calculate an optimal arc angle, comprising the following steps: first, setting a desired value of low radiation dose in lungs $V_5$; substituting the value into an algorithm, $V_{RES}+V_{OR}=V(1-V_5)$, to obtain a $V_{RES}$ value, wherein the values of $V_{OR}$ and V can be obtained from a current radiotherapy plan software; substituting the $V_{RES}$ value into another algorithm to calculate a $\theta_{RES}$ value, wherein the $\theta_{RES}$ value is an unilateral restricted angle (for instance, a $\theta_{RESL}$), and the other unilateral restricted angle (for instance, a $\theta_{RESR}$) can be obtained from the same step as well; addition of the unilateral restricted angle, the other unilateral restricted angle and an optimal arc angle ($\theta_A$) is 360 degrees as a complete circle.

EXAMPLE 2

Figure 6:
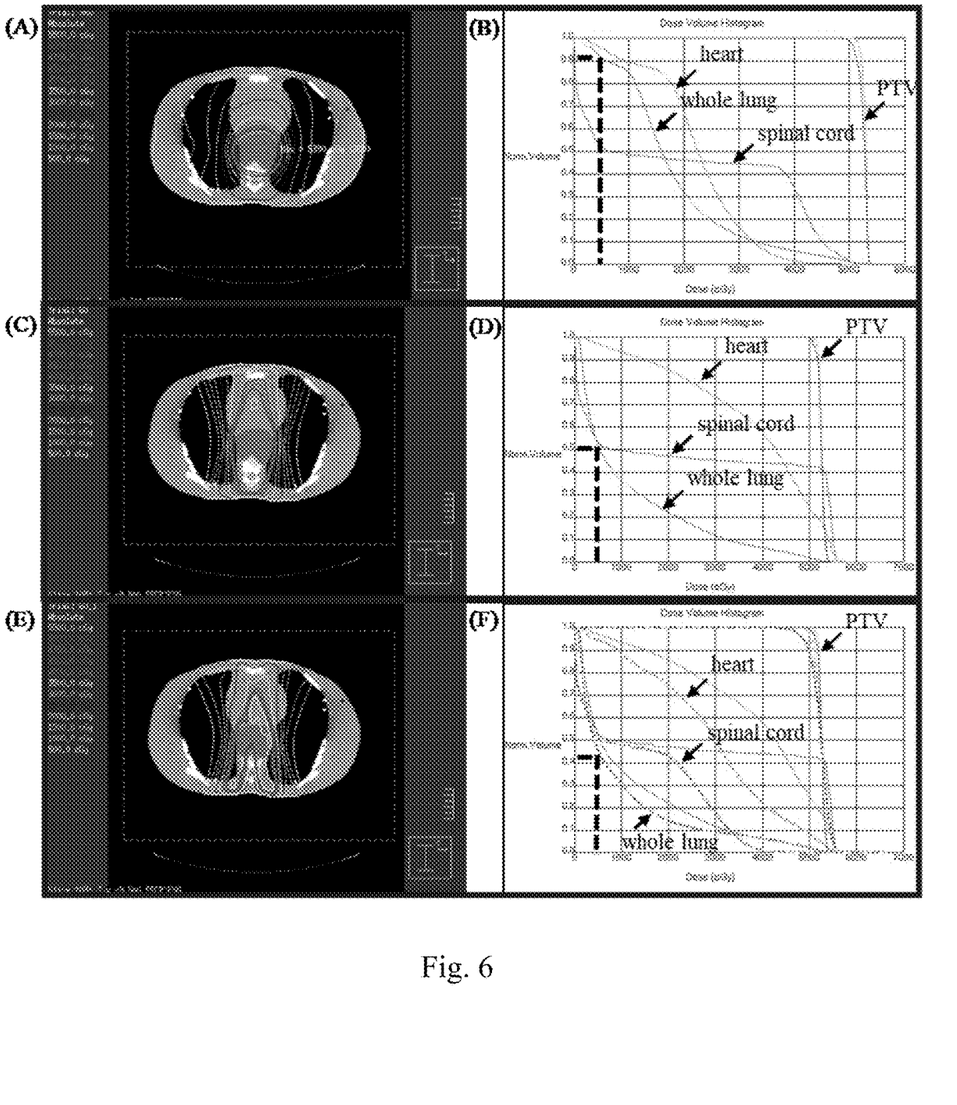
FIG. 6 is a dose distribution diagram and a dose-volume histogram (DVH) of a volumetric modulated arc therapy (VMAT) adopting the present invention, the volume-based algorithms.

The Dose Correlation Between an Optimal Arc Angel and a Lung $V_5$ Value in an Esophageal Cancer Treatment Plan The optimal arc angle obtained from using the method of the present invention is applied to a computer dynamic arc radiotherapy program and thereby compared with a general radiotherapy program to see the difference of the dose distribution in the critical organs. In the general radiotherapy program without the optimal arc angle, the lung $V_5$ value is as high as about 90% (as shown as the light blue curve in FIG. 6B); after applying with the optimal arc angle, the lung $V_5$ value is decreased significantly to 55% (as shown as the light blue curve in FIG. 6D) and the received dose of PTV still remains at an equal level (as shown as the red curve in FIG. 6D); if a minimum dose limit of constraint is given, the lung $V_5$ value can be further lowered to 45% (as shown as the light blue curve in FIG. 6F).

Therefore, the present invention provides an optimal arc angle for quickly optimizing lung dose, V5, in the new dynamic radiation therapy planning system, thereby the excessive time consumption and artificial error caused by repeated tests can be reduced effectively and the optimal arc angle and lung low dose radiation distribution are calculated accurately. Also, the optimal arc angle obtained by the present invention can be used in a radiation therapy planning system immediately, thereby an inexperienced operator can achieve the desired lung dose distribution quickly without repeated tests.

The invention claimed is:

1. A method for rapidly calculating an optimal arc angle of a computer radiation treatment plan for an intrathoracic cancer receiving volumetric modulated arc therapy, comprising:
   substituting a value set comprising a thoracic transverse diameter, a transverse diameter of a radiotherapy planning target volume and a longitudinal length of the radiotherapy planning target volume in a medical image including a thoracic cavity into a restricted volume radius algorithm to calculate a radius of a first unilateral restricted volume and a radius of a second unilateral restricted volume;
   substituting the radius of the first unilateral restricted volume, the radius of the second unilateral restricted volume and a desired value of low radiation dose (5 Gy) in lungs $V_5$ into a restricted volume algorithm to obtain the first unilateral restricted volume;
   substituting the radius of the first unilateral restricted volume, the radius of the second unilateral restricted volume and the desired value of low radiation dose (5 Gy) in lungs $V_5$ into the restricted volume algorithm to obtain the second unilateral restricted volume;
   substituting the first unilateral restricted volume and the second unilateral restricted volume into a volume-based algorithm respectively to obtain a first unilateral restricted angle and a second unilateral restricted angle; and
   subtracting the first unilateral restricted angle and the second unilateral restricted angle from 360 degrees leaves the optimal arc angle.

2. The method of claim 1, wherein the optimal arc angle is an angle that a gantry of a radiotherapy equipment rotates around an isocenter, a centroid of the radiotherapy planning target, to radiate.

3. The method of claim 1, wherein the medical image including a thoracic cavity is a computed tomography or a magnetic resonance image.

4. The method of claim 1, wherein the radiotherapy planning target is an intrathoracic tumor.

5. The method of claim 4, wherein the intrathoracic tumor is an esophageal cancer, lung cancer, or any combination thereof.

6. The method of claim 1, wherein the thoracic transverse diameter, the radiotherapy planning target volume transverse diameter and the longitudinal length of the radiotherapy planning target are measured by Euclid distance.

7. The method of claim 1, wherein the first unilateral restricted volume is a non-irradiated volume in a unilateral lung, and the second unilateral restricted volume is a non-irradiated volume in the other unilateral lung.

8. The method of claim 1, wherein the restricted volume radius algorithm is $$R = \frac{T - E - 4}{2};$$

wherein R is the radius of the first unilateral restricted volume or the radius of the second unilateral restricted volume, T is the thoracic transverse diameter and E is the transverse diameter of the radiotherapy planning target volume.

9. The method of claim 1, wherein the restricted volume algorithm is $V_{RES}+V_{OR}=V(1-V_5)$; wherein $V_{RES}$ is the first unilateral restricted volume or the second unilateral restricted volume, $V_O$ is a unilateral out-of-field volume or the other unilateral out-of-field volume, V is a unilateral lung volume or the other unilateral lung volume, and $V_5$ is the desired value of low radiation dose in lungs.

10. The method of claim 1, wherein the desired value of low radiation dose in lungs $V_5$ is 55% or less.

11. The method of claim 9, wherein the unilateral out-of-field volume is a unilateral lung volume not included in the radiation field in medical image, and the other unilateral out-of-field volume is the other unilateral lung volume not included in radiation field.

12. The method of claim 1, wherein the volume-based algorithm is, $$V_{RES} = \pi R^2 \frac{\theta_{RES}}{360°}(Lt + 4)$$

wherein $V_{RES}$ is the first unilateral restricted volume or the second unilateral restricted volume, R is the radius of the first unilateral restricted volume or the radius of the second unilateral restricted volume, $\theta_{RES}$ is the first unilateral restricted angle and the second unilateral restricted angle, and Lt is the longitudinal length of the radiotherapy planning target of the radiotherapy planning target volume.

* * * * *